United States Patent [19]

de Juan, Jr. et al.

[11] Patent Number: 5,317,938

[45] Date of Patent: Jun. 7, 1994

[54] METHOD FOR MAKING MICROSTRUCTURAL SURGICAL INSTRUMENTS

[75] Inventors: Eugene de Juan, Jr., Phoenix, Md.; Gary W. Jones, Raleigh, N.C.; Susan K. Jones, Raleigh, N.C.; Arnold Reisman, Raleigh, N.C.; Jon Van Winkle, Durham, N.C.

[73] Assignee: Duke University, Durham, N.C.

[21] Appl. No.: 822,021

[22] Filed: Jan. 16, 1992

[51] Int. Cl.⁵ .............................................. B21K 11/00
[52] U.S. Cl. ...................................... 76/104.1; 76/112
[58] Field of Search ............. 76/101.1, 104.1, DIG. 8, 76/112

[56] References Cited

U.S. PATENT DOCUMENTS

| | | | |
|---|---|---|---|
| 4,468,282 | 8/1984 | Neukermans | 156/633 |
| 4,551,192 | 11/1985 | De Milia et al. | 156/345 |
| 4,634,496 | 1/1987 | Mase et al. | 156/643 |
| 4,671,849 | 6/1987 | Chen et al. | 156/643 |
| 4,735,920 | 4/1988 | Stephani et al. | 437/234 |
| 4,740,410 | 4/1988 | Muller et al. | 428/133 |
| 4,808,260 | 2/1989 | Sickafus et al. | 156/644 |
| 4,872,947 | 10/1989 | Wang et al. | 156/643 |
| 4,911,782 | 3/1990 | Brown | 156/633 |
| 4,916,002 | 4/1990 | Carver | 428/139 |
| 4,948,461 | 8/1990 | Chatterjee | 156/643 |
| 4,980,021 | 12/1990 | Kitamura et al. | 156/643 |

FOREIGN PATENT DOCUMENTS

| | | |
|---|---|---|
| 61-210179 | 9/1986 | Japan . |
| WO86/02868 | 5/1986 | PCT Int'l Appl. . |
| 1393611 | 5/1975 | United Kingdom ............... 76/104.1 |

Primary Examiner—Roscoe V. Parker
Attorney, Agent, or Firm—Bell, Seltzer, Park & Gibson

[57] ABSTRACT

A method of making a microsurgical cutter from a flat planar substrate having a top surface and a bottom surface comprises the steps of (a) forming a photoresist mask layer on the top surface in the pattern of the microsurgical instrument, the mask layer having an edge portion formed in a predetermined pattern therein; and then (b) etching isotropically the top surface of the substrate through the top surface to the bottom surface so that the top surface and bottom surface meet at a cutting edge portion, with the cutting edge portion having a configuration corresponding to the edge portion of the mask layer. The substrates may be formed from semiconductor materials such as silicon, silicon carbide, sapphire and diamond.

49 Claims, 3 Drawing Sheets

METHOD FOR MAKING MICROSTRUCTURAL SURGICAL INSTRUMENTS

FIELD OF THE INVENTION

The present invention relates to improved edged medical tools, such as knives, scalpels, saws and the like, and a method for making such tools.

BACKGROUND OF THE INVENTION

In microsurgery such as ophthalmological surgery, small, precision, mechanical structures with ultra-sharp edges are needed. In addition, many shapes and cutting edge variations such as serrated knives and interocular saws are needed for specialized surgery in the region of the eye. Further, it is important that these instruments be made of a mechanically stable material that is both hard and durable.

Conventionally, these edged medical tools are either mass produced from metals such as tungsten, or hand ground from harder materials such as diamond, silicon and sapphire. The disposable metal knives are relatively blunt and wear quickly over time. The nondisposable diamond knives, on the other hand, are expensive and brittle. Further, current techniques of fabricating these harder knives are unable to produce certain cutting edge variations such as serrations that are needed in this type of surgery. Accordingly, there is a substantial need for both edged tools free from the above mentioned problems and ways to make edged tools in a less expensive manner.

Japanese Patent Kokai No. 63-92345 suggests an edged medical tool wherein the surface of the edge tool is provided with a carbonaceous coating layer of a diamond-like crystalline structure having a thickness of 1 to 20 nm which is deposited by the plasma-induced vapor-phase deposition in an atmosphere of a gaseous mixture of hydrogen and a hydrocarbon compound such as methane.

U.S. Pat. No. 4,980,021 to Kitamura et al. suggests the step of etching the diamond-like coating layer formed in a process such as that of the foregoing Kokai with a plasma of hydrogen gas to such an extent that the surface of the edged tool has a roughness of 0.5 to 5 nm. Although this improves the incisiveness of the edged tool, the process starts with an existing base body that was already shaped and, therefore, does not enable the fabrication of knives with serrations and other cutting variations that are needed in opthalmological surgery.

Microelectronic fabrication techniques have been developed in the field of semiconductors. U.S. Pat. No. 4,916,002 to Carver discloses a microminiature tip assembly which is fabricated using photolithography and anisotropic etching. The crystalline form of silicon is taken advantage of by etching along the grain boundaries to form a pit in an silicon substrate. Tungsten is then deposited into the pit to form a sharp tip for use as a scanning tunneling microscope.

Another microfabrication technique disclosed in U.S. Pat. No. 4,740,410 to Muller is a method of producing a micromechanical structure with two or more members measuring less than 1000 micrometers in any linear dimension. The patent technique provides sacrificial layers of material that are later etched away so that the mechanical members become movable relative to each other. Neither of the foregoing, however, addresses the above mentioned problems in the field of microsurgical instruments.

U.S. Pat. No. 4,551,192 to DiMillia et al. discloses the use of a silicon carbide body in a pinchuck formed with microcircuit lithography and U.S. Pat. No. 4,911,782 to Brown discloses a miniature biological chamber made with photolithography, but neither concern cutting instruments.

In view of the foregoing, an object of the present invention is to provide a relatively inexpensive way to mass produce microsurgical knives from a variety of different materials.

Another object of the present invention is to provide a means by which a variety of different microsurgical knives may be produced simultaneously as a single batch.

Still another object of the present invention is to provide microsurgical instruments having a scraper surface.

A further object of the present invention is to provide microsurgical knives in a variety of new and unique shapes, such as serrated knives and concavely shaped knives.

SUMMARY OF THE INVENTION

The foregoing and other objects of the invention are achieved by a method of making a microsurgical cutter from a flat planar substrate having a top surface and a bottom surface. The method comprises the steps of (a) forming a photoresist mask layer on the top surface in the pattern of the microsurgical instrument, the mask layer having an edge portion formed in a predetermined pattern therein; and then (b) etching isotropically the top surface of the substrate through the top surface to the bottom surface so that the top surface and bottom surface meet at a cutting edge portion, with the cutting edge portion having a configuration corresponding to the edge portion of the mask layer. In one embodiment, the bottom surface may also be etched, either simultaneously with or prior to the etching of the top surface.

Also disclosed is a method of making a microsurgical scraper from a flat planar substrate having a top surface and a bottom surface. The method comprises the steps of: (a) providing a photoresist mask layer on the top surface having a pattern of dots formed therein; and then (b) etching isotropically the top surface of the substrate through the pattern of dots to produce a serrated surface therein.

Also disclosed is a microsurgical instrument comprising a flat planar substrate having a top surface and a bottom surface. The top surface has a scraper surface formed therein, with the scraper surface formed from a plurality of adjacent indentations. The adjacent indentations define pointed protrusions projecting upwards from the top surface.

Also disclosed is a microsurgical instrument comprising a flat planar substrate having a top surface, a bottom surface, and at least one cutting edge portion, with the cutting edge portion being either serrated or convex in shape.

BRIEF DESCRIPTION OF THE DRAWINGS

The objects and advantages described herein will be more fully explained by the specification below and the drawings, wherein.

DETAILED DESCRIPTION OF THE INVENTION

A first illustrative embodiment of the present invention is a microsurgical scalpel which has a scraper surface on the top surface thereof. The manufacture of this scalpel is explained below by reference to FIGS. 1 to 4. This process involves a first photolithography and etching step to produce the scraper surface, and a second photolithography and etching step to produce the scalpel itself.

Figure 1:
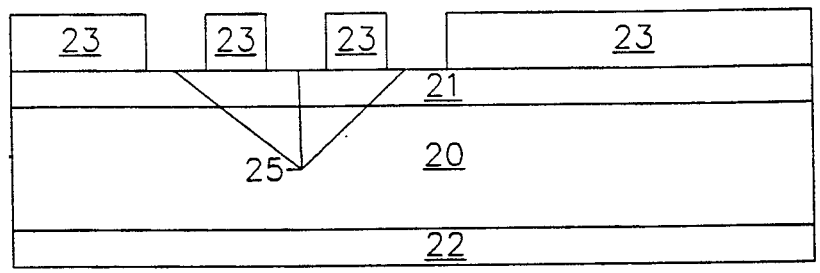
FIGS. 1 through 5 are side sectional views of a substrate during various processing steps of the present invention.
Figure 2:
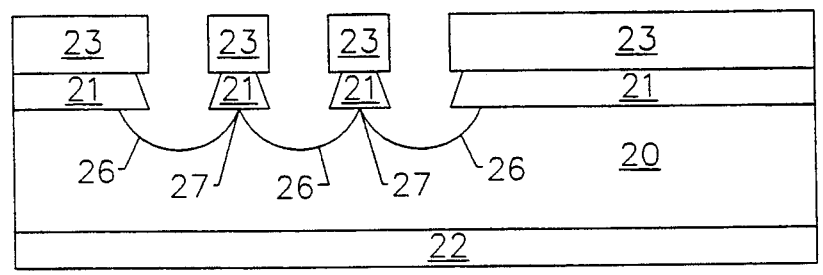

As shown in FIG. 1, a silicon carbide (SiC) wafer 20 has a thin film 21 is deposited on the upper surface and a second thin film 22 optionally deposited on the lower surface thereof by low-pressure chemical vapor deposition (CVD) in accordance with known techniques. See, e.g., W. Feist et al., in *Physics of Thin Films* Vol. 5, pp. 237-314 (G. Hass and R. Thun, Eds. Academic Press, 1969). The wafer 20 is approximately 500 μm thick and 1 inches in diameter. Typically, the wafer will be from about 100 to 600 μm thick, and preferably 200 to 600 μm thick. Thus, several hundred scalpels, scrapers, or other edged cutting instruments, which may be the same or different from one another, can be mass produced from each wafer in a batch process. Note also that, although the material described in this illustrative embodiment is SiC, any appropriate material can be etched into surgical instruments using this process, such as silicon, diamond (both polycrystalline and monocrystalline), sapphire or metals (e.g., stainless steel), with silicon and sapphire currently preferred. Typical materials for thin films 21, 22 include $SiO_2$, $Al_2O_3$ or a Cr-Pt-Cr film, while typical thicknesses range from about 0.5 μm to about 5 μm, with a preferred range of about 1 to 2 μm. Note that thin film 21 is optional if a sufficiently thick or resistant photoresist (discussed bellow) is used.

Following deposition of thin films 21, 22, a patternable photoresist layer 23 approximately 2 to 5 micrometers (μm) thick is deposited on the surface of thin film 21. Virtually any kind of positive or negative patternable resist can be used, as shown in U.S. Pat. No. 4,628,933 (applicants specifically intend that the disclosure of all U.S. Patent References cited herein be incorporated herein by reference). As discussed below, this resist layer will be exposed to patterned ultraviolet light such that only the areas required to be etched will be exposed. Note that, since the geometry of the surgical instrument will ultimately correspond to the pattern of the photoresist, the variety of different surgical instruments which can be manufactured is limited only by the variety of different patterns which can be made.

Figure 6:
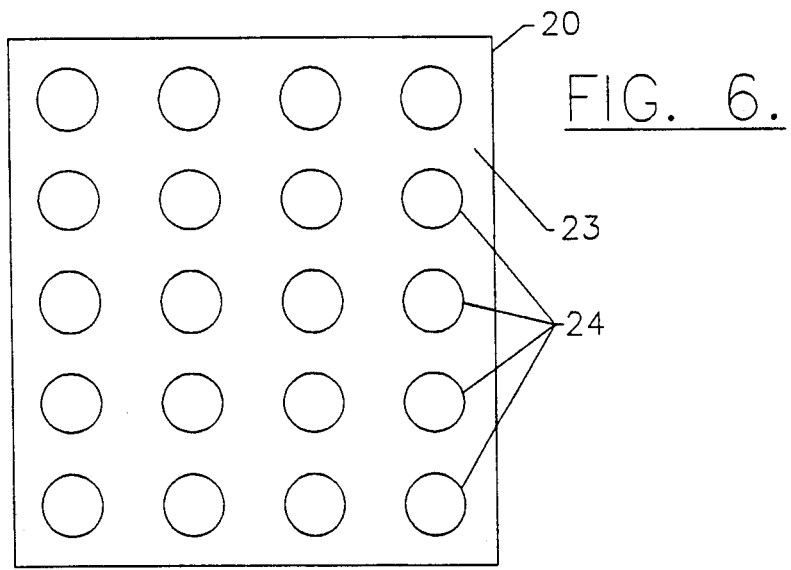
FIGS. 6 and 7 are top plan views of the the substrate illustrated in FIGS. 2 and 4.

In the next step of the process, a pattern of circles 24 (seen in top plan view in FIG. 6) spaced, for example, about 100-105 μm apart, are patterned onto the photoresist to provide a means for creating the scraping portion of the scalpel. Referring back to FIG. 1, the unprotected areas of the $SiO_2$ layer 25 are etched in a buffered hydrofluoric acid solution or, alternatively, they are reactive ion etched (RIE) using conventional means such as described in U.S. Pat. No. 4,671,849. Following this, and turning to FIG. 2, a wet isotropic etchant solution such as, for silicon, an aqueous potassium hydroxide solution or an ethylene diamine pyrocatecol solution, or for sapphire, a sulfuric acid 1:1 solution, is applied to the exposed areas 26 of the SiC wafer substrate 20. This same process can be used on materials such as silicon, diamond and sapphire using etching plasmas conventional in the microprocessing industry. The isotropic solution will tend to etch substantially equally in all directions and, thus, produce a plurality of curved indentations in the exposed areas 26 of the wafer substrate. The isotropic etching continues until the curved indentations formed in the substrate have a radius of, for example, approximately 50 μm. Note that the resist layer and the $SiO_2$ layer will be undercut by the isotropic etching. Therefore, the size of the photolithographic pattern must be sufficiently far apart to accommodate undercutting from both sides, but sufficiently small so that fine points 27 are created between adjacent undercutting etches. The points may be approximately 1-5 μm apart, with the spacing of the photolithographic pattern determining the coarseness or fineness of the scraper surface.

Figure 11:
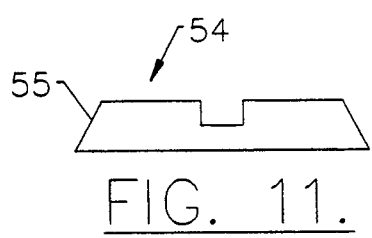
FIG. 11 is a side-sectional view of the intraocular saw shown in FIG. 10, taken along line 11—11 of FIG. 10.
Figure 10:
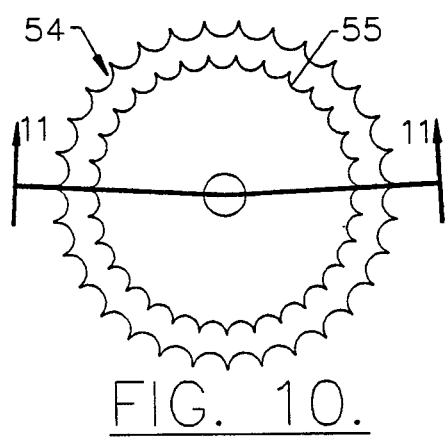
FIG. 10 is a top plan view of an intraocular saw of the present invention.

In addition, the wafer substrate can be subjected to RIE during this first etching step. The RIE method bombards the etching plasma with ions from a source and is well known to those skilled in the art. RIE etches walls that are perpendicular to the surface of the substrate and can be used to create the center of an interocular saw as illustrated in FIGS. 10-11.

Figure 3:
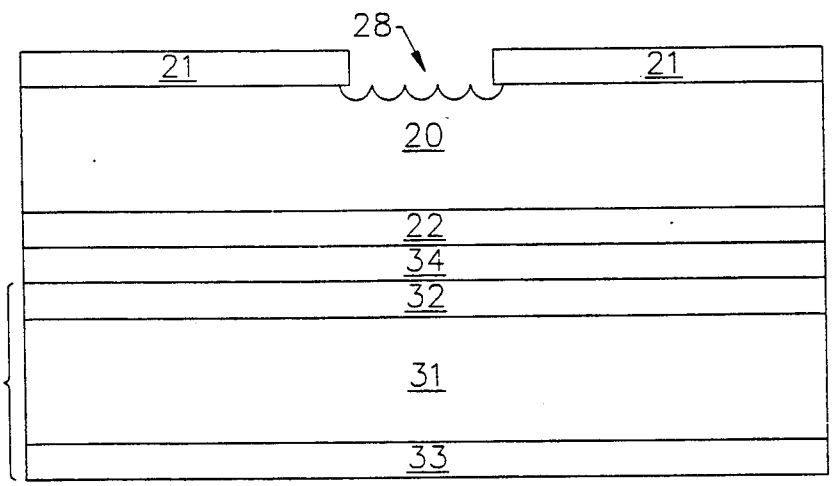

Referring now to FIG. 3, following creation of the serrated scraping surface 28, the photoresist is stripped by means such as a hot $H_2O_2 + H_2SO_4$ or oxygen plasma, in accordance with known techniques. The SiC wafer is then mounted on a carrier substrate 30 such as $SiO_2$ or oxidized silicon (e.g., 525 μm thick silicon 31 with a 1 μm thick oxidized layer 32, 33 on either side) with an adhesive layer 34 such as a controlled polymeric release layer in preparation for the second etching step. In an alternative, preferred approach, a metal film such as a platinum film is deposited directly on the back surface of the wafer substrate by conventional techniques to thereby serve as the carrier.

Figure 4:
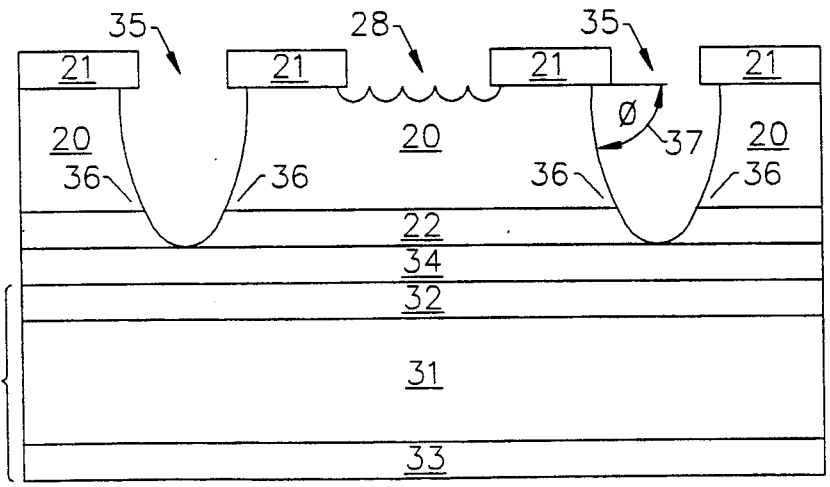
Figure 7:
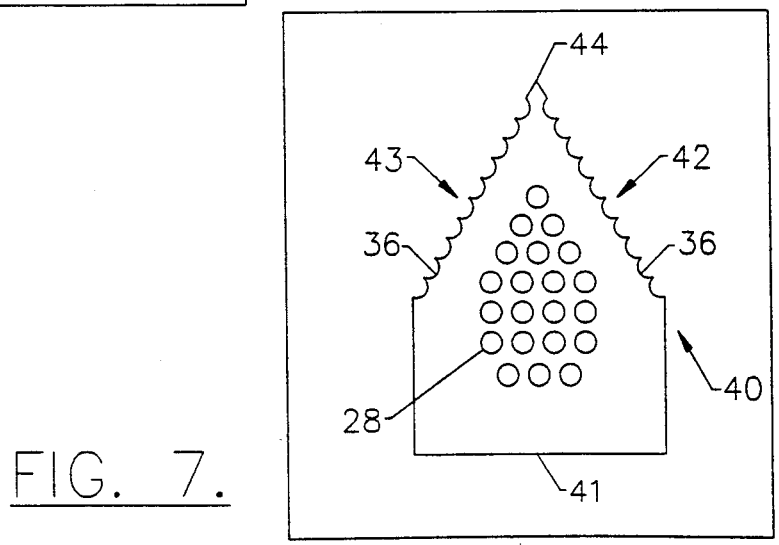

Referring now to FIGS. 4 and 7, the photolithographic process is repeated with a different pattern that will define the perimeter geometry of the instrument and create the knife edge. As will be apparent, the photoresist layer (not shown) applied in this step will overly and protect the serrated surface 28 produced above while the second etching step (discussed below) is being carried out.

In contrast to the first etching step, the second etching step is continued until the curved indentation 35 formed in the top surface of the SiC wafer has reached all the way through the wafer and the top surface meets the bottom surface of the wafer. The radius of the indentation created in the wafer, when examined by side sectional view, will be approximately equal to the thickness of the SiC wafer (150 μm). The isotropic etching will produce a fine edge portion 36 where the top surface meets the bottom surface of the SiC wafer which is the knife edge. Once the SiC wafer has been etched through, continued etching will increase the average angle φ (37) between the top surface of the substrate in the indentation being created by the etch and the plane of the substrate, or the bottom surface of the substrate. Depending on the material employed as the substrate, this angle should be between about 30° and 60°, and more particularly between about 40° and 50°. Ceasing etching before φ is sufficiently large in value will produce a very fine, fragile edge that may break during surgery. Continuing to etch after φ becomes sufficiently large, however, will produce an edge which is too blunt. Hence, once the isotropic etching touches the bottom $SiO_2$ layer, the etching step should only continue for a time sufficient to produce the desired angle φ.

After the second etching step the adhesive layer 34 is dissolved with a suitable solvent, such a acetone, and the surgical instruments float free of the carrier substrate. Note that, if a metal film is employed as the carrier as described above, the metal film is etched away using an aqua regia solution. Masking layers are etched away (with buffered HF solution if $SiO_2$ is used) and the individual instruments are collected. The surgical instruments may be mounted permanently mounted on a disposable handle or removably mounted on a reusable handle. Those skilled in the art will appreciate that several hundred surgical instruments, the same or different, can be produced simultaneously from a single substrate.

As illustrated in FIG. 7, each scalpel 40 may be, for example, about 0.25 to 5 mm wide at the base 41 thereof and from about about 1 to about 7 mm long. The cutting edge or edges 42, 43 on the instruments may typically be from about 0.25 to about 7 mm long depending on whether the geometry of the instrument. The scraper surface 28 manufactured as described above will be formed on the top surface of each scalpel. In the illustrative embodiment, a serrated knife edge is provided along two diagonal lines that come to a point 44. The serrated edges encounter less frictional resistance when slicing through a tissue, and thus are particularly useful for tougher tissue that does not require a perfect straight edge. Insofar as applicants are aware, previous techniques of manufacturing microsurgical scalpels have not produced any type of serrated edge. The present invention, on the other hand, can produce a variety of serrated edges (e.g., saw-toothed edges, convexly serrated edges, and concavely serrated edges). The peaks of the serrations are advantageously extremely close together, for example from about 25 to about 250 μm apart. The present invention also provides for convex cutting edges (i.e., convex with respect to a plan view of the surgical instrument), including convex cutting edges on reverse cutters, which heretofore have also been unavailable.

Figure 5:
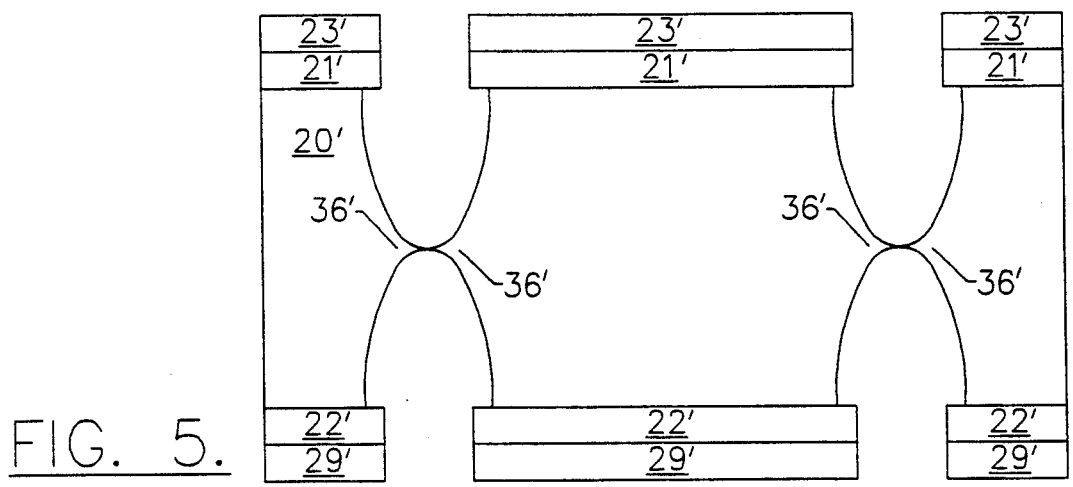

FIG. 5 illustrates an alternative embodiment of the method of the present invention in which the substrate 20' protected on both sides by thin films 21', 22' is etched on both its upper and lower surface. In this embodiment, first photolithographic mask 23' and a second photolithographic mask 29' which is a mirror image (i.e., identical in shape with the first directly overlying the second) of the first photolithographic mask 23' is created and placed on the lower surface of the wafer substrate. Instead of mounting the wafer substrate on a carrier substrate, both sides are subjected to the etching plasma and etching continues, simultaneously or sequentially depending on the etch process, until the two surfaces meet and thereby produce an edge portion 36' which constitutes the knife edge.

Figure 8:
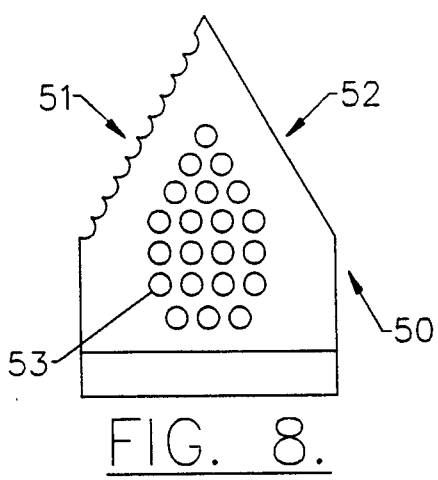
FIG. 8 is a top plan view of a surgical instrument of the present invention.
Figure 9:
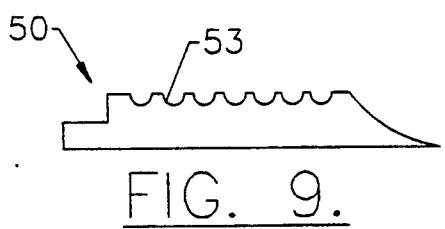
FIG. 9 is a side sectional view of the surgical instrument shown in FIG. 8.
Figure 12:
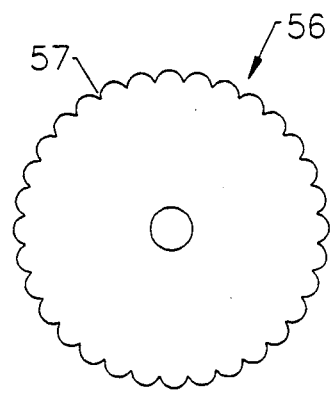
FIGS. 12 to 15 are top plan views of still other embodiments of the present invention.
Figure 13:
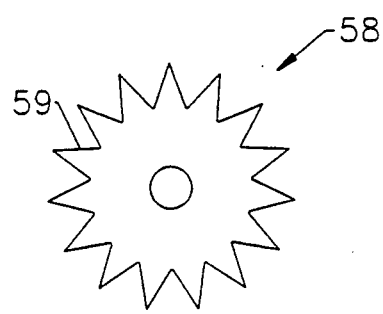
Figure 14:
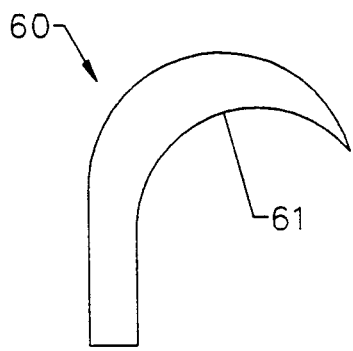
Figure 15:
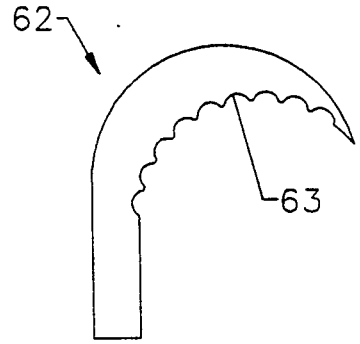

Those skilled in the art may create a surgical instrument of virtually any geometry by simply changing the photolithographic pattern and masking the appropriate parts of the wafer substrate. Numerous alternative embodiments, a few of which are shown in FIGS. 8–15, can be created with this process. For example, patterning a straight edge portion in the photoresist will produce a straight knife edge portion, patterning a convexly curved edge portion in the photoresist will produce a convexly curved knife edge portion, patterning a serrated edge portion in the photoresist will produce a serrated knife edge portion, etc. FIGS. 8–9 illustrate a scalpel 50 with one serrated cutting edge 51 and one straight cutting edge 52 along with a scraper surface 53. Interocular saws with serrated edges as shown in FIGS. 10–13, can be created by using RIE to etch a 0.2 mm square center and then isotropically etching a suitable pattern, such as a circle of dots. This type of surgical cutting tool is useful in slicing off certain tissue in the eye and, has never previously been made with the materials which can be employed in the present process. A saw 54 with a concavely serrated edge 55 is shown in FIGS. 10 and 11, a saw 56 with a convexly serrated edge 57 is shown in FIG. 12, and a saw 58 with a saw-toothed serrated edge 59 is shown in FIG. 13. Additionally, very small scalpels with reverse cutting blades, such as the blade 60 shown in FIG. 14 having concave cutting edge 61, or the blade 62 shown in FIG. 15 having concavely serrated cutting edge 63, may be made with this process. These scalpels can be etched with inner radii much smaller than previous techniques (2 mm) and will enable a surgeon to pull at tissues in the eye with high precision.

The present invention is explained in greater detail in the following non-limiting examples.

EXAMPLE 1

A silicon substrate is etched from a mask that patterned serrated knives, interocular saws, reverse cut scalpels and a variety of other cutting variations (See FIG. 3). Prior to the etching of the silicon, the substrate is patterned (with the above examples) by evaporating a Cr-Pt-Cr (thickness of 30, 500 and 30 nm respectively) film over an inverted profile photoresist. After the metal film is evaporated, the photoresist and metal over the resist is solvent stripped leaving behind the desired mask pattern. After the mask is patterned, the lower portion of the substrate is coated with another evaporated layer of Cr-Pt-Cr of the same thickness. The wafers are then annealed at 1050° C. in oxygen for 60 minutes in final preparation for etching.

The silicon is etched in a bath of KOH solution with a mixture of 100 grams KOH to 100 milliliters of deionized water. The mixture is then heated to 75° C. The wafers are placed in the bath and etched at a rate of 75 μm/minute with a continuous stirring motion to prevent etchant stagnation. This produces an isotropic etch profile of approximately 45°, providing an ideal cutting edge. Following the etch, the knives are removed from the bath and placed in aqua regia to remove the platinum based mask.

EXAMPLE 2

Sapphire knives are fabricated in a manner similar to that described in Example 1 above. The etch mask is made by the lift-off method, in which the mask material is 500 nm of Pt over 50 nm of Cr. The wafer is then annealed at 1050° C. in oxygen for 60 minutes in preparation for the etch. In this case, the sapphire wafer is etched from both sides as shown in FIG. 1E.

The sapphire wafers are etched in a platinum vessel containing a 1 to 1 Sulfuric-Phosphoric acid solution. The solution is heated to 285° C. and etched at a rate of approximately 5 $\mu$m/hour. After the etch is completed, the sapphire knives are removed and placed in aqua regia to remove the Pt-Cr mask. As in example 1, the sapphire knives have a sharp cutting edge.

The foregoing examples are illustrative of the present invention, and is not to be construed as limiting thereof. The invention is defined by the following claims, with equivalents of the claims to be included therein.

That which is claimed is:

1. A method of making a microsurgical cutter from a flat planar substrate having a top surface and a bottom surface, comprising the steps of:
   (a) forming a photoresist mask layer on said top surface in the pattern of the microsurgical instrument, said mask layer having an edge portion formed in a predetermined pattern therein; and then
   (b) etching isotropically the top surface of said substrate through said top surface to said bottom surface so that said top surface and bottom surface meet at a cutting edge portion, said cutting edge portion having a configuration corresponding to said edge portion of said mask layer.

2. A method according to claim 1, wherein said etching step is followed by the step of removing said photoresist mask layer from said substrate.

3. A method according to claim 1, wherein said substrate comprises a semiconductor material.

4. A method according to claim 1, wherein said substrate is selected from the group consisting of silicon, silicon carbide, diamond, and sapphire.

5. A method according to claim 1, wherein said cutting edge portion has a length of from about 0.25 to about 10 millimeters.

6. A method according to claim 1, wherein said substrate has a thickness of from about 100 to about 600 micrometers ($\mu$m).

7. A method according to claim 1, wherein said substrate has a thickness of from about 200 to 300 $\mu$m.

8. A method according to claim 1, wherein, following said etching step, said top surface and said bottom surface intersect at said cutting edge portion at an angle of from about 30 to 60 degrees.

9. A method according to claim 1, wherein said etching step is a wet etching step.

10. A method according to claim 1, wherein said mask layer edge portion is serrated in shape.

11. A method according to claim 1, wherein said mask layer edge portion is concave in shape.

12. A method of making a microsurgical cutter according to claim 1 which further comprises, prior to step (b), forming a second photoresist mask layer on said bottom surface in the pattern of the microsurgical instrument, said mask layer having a second edge portion formed in a predetermined pattern therein.

13. A method of making a microsurgical cutter according to claim 12 wherein step (b) comprises etching isotropically both the top surface of said substrate and the bottom surface of said substrate simultaneously so that said top surface and said bottom surface meet at a cutting edge portion.

14. A method of making a microsurgical cutter according to claim 12 which further comprises, following step (b), etching isotropically the bottom surface of said substrate so that said bottom surface and said top surface meet at a cutting edge portion.

15. A method of making a microsurgical scraper from a flat planar substrate having a top surface and a bottom surface, comprising the steps of:
   (a) masking said top surface to produce a pattern of dots on said top surface; and then
   (b) etching the top surface of said substrate through said pattern of dots to produce a serrated scraper surface with pointed projections.

16. A method according to claim 15, wherein said etching step (b) is followed by the steps of:
   (c) masking said top surface in the pattern of the microsurgical instrument, said mask layer overlying said serrated scraper surface, to expose an edge portion formed in a predetermined pattern therein; and then
   (d) etching the top surface of said substrate through said top surface to said bottom surface so that said top surface and said bottom surface meet at a cutting edge portion, said cutting edge portion having a configuration corresponding to said edge portion of said mask layer.

17. A method according to claim 15, wherein said substrate comprises a semiconductor material.

18. A method according to claim 15, wherein said substrate is selected from the group consisting of silicon, silicon carbide, diamond, and sapphire.

19. A method according to claim 15, wherein said cutting edge portion has a length of from about 0.25 to about 10 millimeters.

20. A method according to claim 15, wherein said substrate has a thickness of from about 100 to about 600 $\mu$m.

21. A method according to claim 15, wherein said substrate has a thickness of from about 200 to 300 $\mu$m.

22. A method according to claim 16, wherein, following said etching step (d), said top surface and said bottom surface intersect at said cutting edge portion at an angle of from about 30 to 60 degrees.

23. A method according to claim 16, wherein said etching step (d) is a wet etching step.

24. A method according to claim 16, wherein said second mask layer edge portion is serrated in shape.

25. A method of making a microsurgical cutter from a flat planar substrate having a first side and a second side comprising the steps of:
   (a) masking said first side to define a first portion of said first side;
   (b) masking said second side to define a second portion of said second side;
   (c) etching said substrate through said first and second defined portions to form a cutting edge which extends through said substrate from said first side to said second side.

26. A method according to claim 25 wherein the etching of step (c) comprises sequentially etching the first side of said substrate and then etching the second side of said substrate, through said first and second sides so that said first side and said second side meet at a cutting edge portion.

27. A method according to claim 25 wherein step (c) comprises simultaneously etching both the first side and the second side of said substrate, through said first and second sides so that said first side and said second side meet at a cutting edge portion.

28. A method according to claim 25, wherein said etching step (c) is followed by the step of removing any masking from said substrate.

29. A method according to claim 25, wherein said substrate comprises a semiconductor material.

30. A method according to claim 25, wherein said substrate is selected from the group consisting of silicon, silicon carbide, diamond, and sapphire.

31. A method according to claim 25, wherein said cutting edge portion has a length of from about 0.25 to about 10 millimeters.

32. A method according to claim 25, wherein said substrate has a thickness of from about 100 to about 600 micrometers ($\mu$m).

33. A method according to claim 25, wherein said substrate has a thickness of from about 200 to 300 $\mu$m.

34. A method according to claim 25, wherein, following said etching step, said first side and said second side intersect at said cutting edge portion at an angle of from about 30 to 60 degrees.

35. A method according to claim 25, wherein said etching step is a wet etching step.

36. A method according to claim 25, wherein said masking steps define portions of said substrate which are serrated in shape.

37. A method according to claim 25, wherein said masking steps define portions of said substrate which are concave in shape.

38. A method of making a microsurgical cutter from a flat planar substrate having a top surface and a bottom surface, comprising the steps of:
   (a) forming mask layer means on said top surface for masking said top surface in the pattern of the microsurgical instrument, said mask layer means having an edge portion formed in a predetermined pattern therein; and then
   (b) etching isotropically the top surface of said substrate through said top surface to said bottom surface so that said top surface and bottom surface meet at a cutting edge portion, said cutting edge portion having a configuration corresponding to said edge portion of said mask layer means.

39. A method according to claim 38, wherein said etching step is followed by the step of removing said mask layer means from said substrate.

40. A method according to claim 38, wherein said substrate comprises a semiconductor material.

41. A method according to claim 38, wherein said substrate is selected from the group consisting of silicon, silicon carbide, diamond, and sapphire.

42. A method according to claim 38, wherein said cutting edge portion has a length of from about 0.25 to about 10 millimeters.

43. A method according to claim 38, wherein said substrate has a thickness of from about 100 to about 600 micrometers ($\mu$m).

44. A method according to claim 38, wherein said substrate has a thickness of from about 200 to 300 $\mu$m.

45. A method according to claim 38, wherein, following said etching step, said top surface and said bottom surface intersect at said cutting edge portion at an angle of from about 30 to 60 degrees.

46. A method according to claim 38, wherein said etching step is a wet etching step.

47. A method according to claim 38, wherein said mask layer means edge portion is serrated in shape.

48. A method according to claim 38, wherein said mask layer means edge portion is concave in shape.

49. A method according to claim 38 which further comprises, prior to step (b), forming a second mask layer means on said bottom surface for masking said bottom surface in the pattern of the microsurgical instrument, said second mask layer means having a second edge portion formed in a predetermined pattern therein and wherein step (b) comprises etching isotropically both the top surface of said substrate and the bottom surface of said substrate so that said top surface and said bottom surface meet at a cutting edge portion.

* * * * *